US008977342B2

(12) United States Patent
Hoheisel

(10) Patent No.: US 8,977,342 B2
(45) Date of Patent: Mar. 10, 2015

(54) MEDICAL INTERVENTION DEVICE

(75) Inventor: Martin Hoheisel, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1607 days.

(21) Appl. No.: 12/313,567

(22) Filed: Nov. 21, 2008

(65) Prior Publication Data

US 2009/0149740 A1 Jun. 11, 2009

(30) Foreign Application Priority Data

Dec. 11, 2007 (DE) .......................... 10 2007 059 599

(51) Int. Cl.
*A61B 5/05* (2006.01)
*A61B 19/00* (2006.01)
*A61B 17/00* (2006.01)

(52) U.S. Cl.
CPC ............ *A61B 19/5244* (2013.01); *A61B 19/46* (2013.01); *A61B 2017/00694* (2013.01); *A61B 2019/464* (2013.01); *A61B 2019/4894* (2013.01); *A61B 2019/5248* (2013.01); *A61B 2019/5251* (2013.01); *A61B 2019/5289* (2013.01)
USPC .......................................... 600/424; 606/130

(58) Field of Classification Search
CPC ............... A61B 19/5244; A61B 19/46; A61B 2017/00694; A61B 2019/464; A61B 2019/4894; A61B 2019/5248; A61B 2019/5251; A61B 2019/5289
USPC ......... 600/117, 118, 173, 407–424, 573, 578; 606/130
See application file for complete search history.

(56) References Cited

U.S. PATENT DOCUMENTS

| 5,836,869 | A | * | 11/1998 | Kudo et al. | .................... 600/173 |
| 6,036,637 | A | * | 3/2000 | Kudo | ............................ 600/173 |
| 6,611,141 | B1 | | 8/2003 | Schulz et al. | |
| 7,518,502 | B2 | * | 4/2009 | Austin et al. | ............... 340/539.1 |
| 7,672,741 | B2 | * | 3/2010 | Ohnishi et al. | .................. 700/63 |
| 7,713,205 | B2 | * | 5/2010 | Fu et al. | ......................... 600/443 |
| 7,841,981 | B2 | * | 11/2010 | Kawano et al. | ............... 600/118 |
| 8,126,736 | B2 | * | 2/2012 | Anderson et al. | ................. 705/2 |
| 2003/0088302 | A1 | * | 5/2003 | Shirakawa et al. | ........... 607/122 |

(Continued)

FOREIGN PATENT DOCUMENTS

| DE | 10 2005 037 426 A1 | 2/2007 |
| DE | 10 2006 049 575 A1 | 4/2008 |
| WO | 2005087114 A1 | 9/2005 |

OTHER PUBLICATIONS

Haid, Markus; Inertial low cost indoor navigation and the possibilities for medical applications; vol. 50, Supplementary vol. 1, Part 2, 2005; Magazine; 2005.

(Continued)

*Primary Examiner* — Sanjay Cattungal

(57) ABSTRACT

The invention relates to a device for a medical intervention in or on moving tissue of a living being, said device having a medical instrument provided for the intervention, a position detection system by means of which the position of the medical instrument in the body of the living being can be determined, and at least one acceleration sensor for recording at least one movement of the instrument caused by the moving tissue. The invention also relates to a medical instrument for a medical intervention in or on moving tissue of a living being, said medical instrument having at least one acceleration sensor and a sensor of a position detection system, as well as to an operating method for the device.

14 Claims, 1 Drawing Sheet

(56) References Cited

U.S. PATENT DOCUMENTS

| | | | |
|---|---|---|---|
| 2005/0057684 A1* | 3/2005 | Tamakoshi | 348/375 |
| 2007/0016067 A1* | 1/2007 | Webster et al. | 600/464 |
| 2007/0021738 A1* | 1/2007 | Hasser et al. | 606/1 |
| 2007/0112466 A1* | 5/2007 | Ohnishi et al. | 700/260 |
| 2007/0167747 A1 | 7/2007 | Borgert et al. | |
| 2007/0270686 A1* | 11/2007 | Ritter et al. | 600/424 |
| 2008/0132909 A1* | 6/2008 | Jascob et al. | 606/130 |
| 2009/0018403 A1* | 1/2009 | Black et al. | 600/300 |
| 2009/0224935 A1* | 9/2009 | Kagermeier et al. | 340/825.72 |
| 2009/0299142 A1* | 12/2009 | Uchiyama et al. | 600/118 |
| 2010/0183196 A1* | 7/2010 | Fu et al. | 382/103 |
| 2010/0217099 A1* | 8/2010 | LeBoeuf et al. | 600/301 |
| 2010/0217118 A1* | 8/2010 | Muhlsteff et al. | 600/425 |
| 2010/0312129 A1* | 12/2010 | Schecter | 600/508 |
| 2011/0160589 A1* | 6/2011 | Fu et al. | 600/443 |
| 2014/0081128 A1* | 3/2014 | Verard et al. | 600/424 |

OTHER PUBLICATIONS

CAS innovations AG; Precision in Therapy Planning and Navigation Cappa Navigation System; http://www.cas-innovations.de/cms/index.php?id=6&L=1; Others; 2006.

NDI; NDI Products & Accessories Polaris®; Internetseiten http://www.ndigital.com/; Others; 2006.

NDI; NDI Polaris® data sheets; aus dem Internet; 2002/2004; Others; 2002.

NDI; NDI Products & Accessories Aurora®; Internetseiten http://www.ndigital.com/; Others; 2006.

NDI; NDI Aurora® ® Electromagnetic Tracking System; Broschüre aus Internet; Others; 2005.

\* cited by examiner

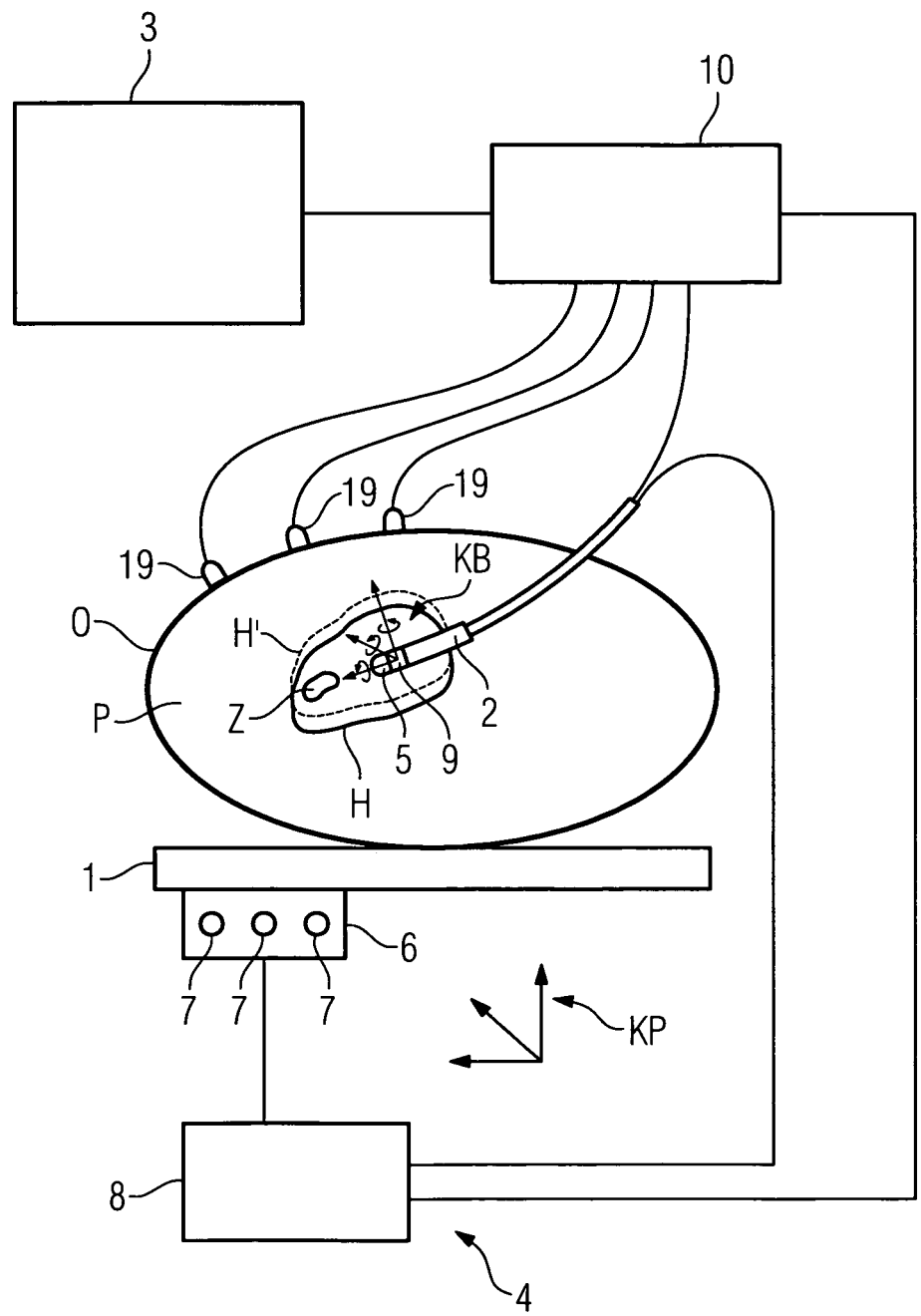

MEDICAL INTERVENTION DEVICE

CROSS REFERENCE TO RELATED APPLICATIONS

This application claims priority of German application No. 10 2007 059 599.0 filed Dec. 11, 2007, which is incorporated by reference herein in its entirety.

FIELD OF THE INVENTION

The invention relates to a device for a medical intervention in or on moving tissue of a living being as well as to a medical instrument for a medical intervention in or on moving tissue of a living being. The invention also relates to an operating method for the said device for a medical intervention in or on moving tissue of a living being.

BACKGROUND OF THE INVENTION

In medical interventions on or in bodies of living beings in which one or more than one medical instrument is introduced at least partially into the body of the living being such that the instruments are at least partially no longer directly visible, increasing use is made of position detection systems, referred to as navigation and tracking systems, by means of which the positions of the instruments in the body of the living being are detected and can be superimposed on a 2D or 3D image of the inside of the body of the living being. The image of the inside of the living being's body is usually a preoperatively recorded X-ray, ultrasound or magnetic resonance image. The superimposing of the instrument or instruments on the image of the inside of the living being's body enables a physician performing the medical intervention to handle or navigate the instruments, which may be for example catheters, puncture needles, endoscopes, etc., with the aid of an image.

Examples that may be cited of position detection systems or navigation and tracking systems are the CAPPA system of the company CAS Innovations AG, the Polaris optical navigation and tracking system of the company Northern Digital as well as the Aurora electromagnetic navigation and tracking system of the company Northern Digital. By means of position detection systems or navigation and tracking systems of this kind the positions of instruments in the body of a living being can be determined and, as already mentioned, superimposed onto a 3D image or a 3D image dataset for example or correlated with the latter and visualized on a display unit.

A system for navigating a medical instrument in an operating region of a living being is described in US 2007/0270686 A1, wherein acceleration sensors associated with a navigation system are disposed in the distal end of the medical instrument in order to determine the current position of the medical instrument at any given time. Based on the determined position in each case, the medical instrument can be navigated in the body of the living being.

The post-published German patent application DE 10 2006 049 575 A1 discloses a detecting device for detecting an object in up to three dimensions by means of X-rays. The device additionally comprises a location sensor for determining the position of a medical instrument and a movement sensor, e.g. an accelerometer, by means of which a movement of a patient can be registered.

A device and a method for fusing image datasets are also known from DE 10 2005 037 426 A1. Movements of a patient can be registered with the aid of a movement sensor, e.g. an accelerometer, and taken into account during the image fusion.

However, involuntary movements of a living being, which are caused for example by the breathing and heartbeat of the living being, are problematic for the use of navigation and tracking systems during medical interventions. Thus, during a medical intervention in or on moving tissue of a living being, e.g. a moving organ of a living being, it is not only the target region or target tissue of the intervention that moves, but also the instrument used for the intervention, as a result of which the position determination or tracking of the used instrument, and consequently the navigation of the instrument, is rendered more difficult or, as the case may be, imprecise.

SUMMARY OF THE INVENTION

The object underlying the invention is therefore to disclose a device, a medical instrument and a method of the kind cited in the introduction such that the determination of the position of a medical instrument in the body of a living being is possible relatively precisely.

The object relating to the device is achieved according to the invention by means of a device for a medical intervention in or on moving tissue of a living being, said device having a medical instrument provided for the intervention, a position detection system by means of which the position of the medical instrument in the body of the living being can be determined, at least one acceleration sensor for detecting at least one movement of the instrument caused by the moving tissue, and a computing device by means of which, based on position data of the instrument determined by means of the position detection system and at least one measured value of the at least one acceleration sensor that was preferably recorded at essentially the same time as the position data, the position of the medical instrument in or on the moving organ is determined or, as the case may be, corrected by means of the at least one item of position data of the instrument determined by means of the position detection system using at least one recorded measured value of the at least one acceleration sensor. It is therefore proposed according to the invention to provide at least one acceleration sensor for registering preferably the movements of an instrument directly or indirectly caused by the moving tissue in order to determine, with the aid of the registered movements of the instrument, the actual position of the instrument during an intervention in or on moving tissue in the body of the living being. In the process, based on the measurement of the acceleration and/or rotational acceleration of the tissue or instrument relative to a previous position of the tissue or instrument by means of the acceleration sensor, the movement or, as the case may be, distance traveled by the instrument in the respective measurement direction, be it an essentially linear movement or rotary movement, can be quantitatively established and used to determine the position of the instrument. In this way it is therefore possible to track the movements of the instrument in or on the moving tissue irrespective of disruptive movements of the tissue. Incidentally, a suitable acceleration sensor is described for example by Markus Haid in "Inertial low cost indoor navigation and the possibilities for medical applications", published in the German biomedical engineering journal Biomedizinische Technik, Vol. 50, Supplementary vol. 1, Part 2, 2005, pages 955-956.

For that purpose the device has a computing device by means of which, based on position data of the instrument determined by means of the position detection system and at least one measured value of the at least one acceleration sensor that was preferably recorded at essentially the same time as the position data, the position of the medical instrument in or on the moving organ is determined or, as the case may be, corrected by means of the at least one item of position data of the instrument determined by means of the position detection system using at least one measured value of the at least one acceleration sensor that was preferably recorded at essentially the same time as the position data. Usually a plurality of position data of the instrument are corrected in each case using measured values of the at least one acceleration sensor. In other words, the movements of the instrument caused by the moving tissue are recorded with the aid of the acceleration sensor, quantified and used for determining the position of the medical instrument or, as the case may be, for correcting the position data determined by means of the position detection system. In this way the actual position of the instrument, for example the actual position of the tip of the instrument, can be established relatively easily and quickly.

If the respective positions of the medical instrument and hence the movement curve of the medical instrument, in particular the tip of the medical instrument, are known, an image of the medical instrument for example can be superimposed relatively precisely on a preoperatively recorded static image of the moving organ per se, with the movement of the medical instrument being factored out or, as the case may be, taken into account.

If movements of the instrument are to be recorded in a plurality of spatial directions and/or in a plurality of rotational directions, then provided that one acceleration sensor according to a variant of the invention has a measured value recorder for recording a movement in a spatial direction or in a rotational direction, a plurality of acceleration sensors, possibly up to six or more acceleration sensors, will be required.

According to a variant of the invention, however, an acceleration sensor can also have a plurality of measured value recorders, with one measured value recorder being provided in each case for recording a movement in a spatial direction or in a rotational direction. Ideally, one acceleration sensor can have up to six or more measured value recorders, of which for example three measured value recorders record measured values in the three spatial directions and for example three measured value recorders record measured values in the three rotational directions around the axes of the three spatial directions.

Preferably at least one acceleration sensor is disposed in a defined manner on or in the instrument, preferably at, in or in the region of the tip of the instrument. Ideally said acceleration sensor will have a plurality of measured value recorders.

If the acceleration sensor is relatively large compared with the instrument, such that it cannot be disposed, or can be disposed only with difficulty, on or in the instrument, then alternatively the acceleration sensor can also be disposed in a defined manner in proximity to the instrument in order in this way to indirectly record the movements of the instrument via the movements of the moving tissue. In this case the at least one acceleration sensor is usually disposed in a defined manner on the surface of a living being's body. It is therefore possible to determine the movements of an instrument caused by moving tissue either only by means of one acceleration sensor having a corresponding number of measured value recorders and being disposed in or on the instrument, or by means of a plurality of acceleration sensors disposed in or on the instrument. Alternatively the movements of the instrument can additionally be determined for example by means of one or more acceleration sensors disposed on the surface of the living being's body. However, it is also possible to determine the movements of the instrument only by means of one or more acceleration sensors disposed for example on the surface of a living being's body.

An embodiment of the invention provides that the position detection system is an optical or electromagnetic position detection system, wherein according to a further variant of the invention at least one sensor of the position detection system is disposed in a defined manner in or on the instrument. In this way the positions of the medical instrument in the body of the living being can be determined initially by means of the position detection system. The determined position data are then, as already mentioned, corrected if necessary using the recorded measured values of the acceleration sensor or sensors having a higher measuring rate in order to be able to determine the actual position of the instrument in the body of the living being as precisely and as quickly as possible when the instrument is moving in the course of the medical intervention in or on moving tissue together with the moving tissue.

According to a further embodiment of the invention the instrument is a catheter or a puncture needle.

The object relating to the medical instrument is achieved by means of a medical instrument for a medical intervention in or on a moving organ of a living being, said medical instrument having at least one acceleration sensor and a sensor of a position detection system.

As already mentioned, the acceleration sensor can have one measured value recorder for recording a movement in a spatial direction or rotational direction or else a plurality of measured value recorders, one measured value recorder in each case being provided for recording a movement in a spatial direction or rotational direction.

Preferably the medical instrument is a catheter or a puncture needle, with the at least one acceleration sensor preferably being disposed essentially in, at or in the region of the tip of the instrument.

The object of the invention relating to the operating method is achieved by means of an operating method for a device for a medical intervention in or on moving tissue of a living being as described previously, wherein with the operating method position data of the instrument in the body of the living being are determined by means of the position detection system during a medical intervention in or on the moving tissue by means of the instrument, wherein measured values are recorded by means of the at least one acceleration sensor, and wherein, based on an item of position data of the instrument determined by means of the position detection system and at least one measured value of the at least one acceleration sensor that was recorded preferably at essentially the same time as the position data, the position of the medical instrument in or on the moving organ is determined or, as the case may be, wherein at least one item of determined position data of the instrument is corrected in order to take account of at least one movement of the instrument caused by the moving tissue with the aid of at least one recorded measured value of the at least one acceleration sensor.

As already described previously, a relatively precise and quick correction of the position data of the instrument determined by means of the position detection system is possible by means of the measured values of the at least one acceleration sensor in order to take account of the movements of the instrument caused by the moving tissue.

According to a variant of the invention, an image of the instrument or even only a marker of the location of the instrument is superimposed on an image of the moving tissue, based on corrected position data of the instrument. In this case the image of the instrument is preferably superimposed during the entire navigation of the instrument in the body of the living being so that the current position and orientation of the instrument in or, as the case may be, relative to tissue of interest are always available to the physician performing the medical intervention in an image of the moving tissue or, as the case may be, tissue of interest. The image is preferably a 2D or 3D image.

According to a further variant of the invention, the recordings of the position data by means of the position detection system and the recordings of the measured values by means of the at least one acceleration sensor are synchronized with one another so that the position data of the position detection system and the associated measured values of the acceleration sensors in each case can be correlated with one another.

BRIEF DESCRIPTION OF THE DRAWINGS

An exemplary embodiment of the invention is shown in the attached schematic drawing.

DETAILED DESCRIPTION OF THE INVENTION

According to the FIGURE, a schematically represented patient P is positioned on a patient positioning device 1. A medical intervention is to be performed with the aid of a medical instrument on moving tissue inside the body of the patient P. In the case of the present exemplary embodiment, the moving tissue of the patient P is the heart H of the patient P, the movements of the heart H being indicated by means of the dashed outline H'. In the case of the present exemplary embodiment, the medical instrument is a catheter 2, an ablation catheter for example, which has been advanced in a manner known per se e.g. via veins or arteries of the patient P into the heart H of the patient P. Inside the heart H, target tissue Z of interest is to be examined or, as the case may be, treated.

Because the catheter 2, after having been introduced into the body of the patient P, is no longer visible to a physician performing the medical intervention, the medical intervention is performed with the aid of an image of the heart H of the patient P displayed on a display device 3. The image can be generated preoperatively or intraoperatively by means of an ultrasound device, an X-ray device or a magnetic resonance device. The image displayed on the display device 3 can be a 2D image or else a 3D image. Furthermore, the image displayed on the display device 3 can be an overlaid or merged image of the heart H of the patient P. For example, the displayed image can be the result of the overlaying of an X-ray image and an ultrasound image.

For the purpose of navigation, an image of the catheter 2 is preferably superimposed on said image of the heart H of the patient P displayed on the display device 3. Toward that end, an electromagnetic position detection system 4 is provided which, in addition to a sensor 5 disposed in a defined manner in the tip of the catheter 2, has a transmitter unit 6 disposed in a defined manner on the patient positioning device 1 and having, in the case of the present exemplary embodiment, three transmitters 7, each of which generates an electromagnetic field. The transmitter unit 6 and the electromagnetic sensor 5 are connected to a computing device 8 of the electromagnetic position detection system 4 such that the sensor 5 can be detected in the electromagnetic fields of the transmitters 7 and in particular its positions in a coordinate system KP assigned to the electromagnetic position detection system 4 can be determined by means of the computing device 8. Thus, the positions of the electromagnetic sensor 5 and accordingly also of the catheter 2 can be determined in the coordinate system KP of the electromagnetic position detection system 4 and indicated. Moreover, the image of the heart H of the patient P displayed on the display device 3 is registered by means of the electromagnetic position detection system 4, which means that the coordinate transformation from the coordinate system KP of the electromagnetic position detection system 4 into the image coordinate system assigned to the image displayed on the display device 3 is known, so that an image of the catheter 2 can be superimposed on the image of the heart H of the patient P displayed on the display device 3.

As already mentioned, the heart H is a moving organ, so the catheter 2 introduced into the heart H moves at least in a certain manner in concert with the heart H. This leads to inaccuracies in position determination by means of the electromagnetic position detection system 4, which is why it is proposed according to the invention to dispose an acceleration sensor 9 having a higher measurement rate in a defined manner in the tip of the catheter 2 in addition to the electromagnetic sensor 5. In the case of the present exemplary embodiment, the acceleration sensor 9 has six measured value recorders in total, with one measured value recorder being provided in each case for recording a movement in one of the three spatial directions of the coordinate system KB assigned to the acceleration sensor 9 and with one measured value recorder being provided in each case for recording a movement in one of the three rotational directions around the coordinate axes of the coordinate system KB assigned to the acceleration sensor 9.

In the course of the medical intervention, measured values relating to the three spatial directions and the three rotational directions of the coordinate system KB are accordingly recorded by means of the acceleration sensor 9, with quantitative values or, as the case may be, movements of the catheter 2 in the corresponding directions relative to a previously assumed position of the catheter 2 being determined from the measured values in the form of essentially linear accelerations and rotational accelerations. Since the acceleration sensor 9 is disposed in a defined manner on the catheter 2 as well as relative to the electromagnetic sensor 5 of the position detection system 4, these determined quantitative values relating to the movements of the catheter 2 can be used to correct the position data determined by means of the electromagnetic position detection system 4 with regard to the movements of the catheter 2 caused by the movements of the heart H. The position of the catheter 2 can therefore be determined based on the measured values of the acceleration sensor 9 or, as the case may be, on the quantitative values and the position data determined by means of the electromagnetic position detection system 4.

Said position determination or, as the case may be, correction is performed by a computing device 10 which is operated by means of a corresponding piece of software and which is connected not only to the acceleration sensor 9 but also to the computing device 8 of the electromagnetic position detection system 4. Accordingly, the computing device 10 has available to it the position data of the catheter 2 determined by means of the electromagnetic position detection system 8 as well as the measured values of the acceleration sensor 9. In this case the computing device 10 also synchronizes the recording of the position data by means of the electromagnetic position detection system 4 and the recording of the measured values by means of the acceleration sensor 9, with the result that position data determined by means of the electromagnetic position detection system 4 and the associated measured values determined by means of the acceleration sensor 9 in each case are correlated with one another or, as the case may be, computed with one another.

Finally, also based on the determined position or, as the case may be, the corrected position data of the catheter 2, an image of the catheter 2 or even only a marker of the location of the catheter 2 is superimposed with the aid of the computing device 10 onto the image of the heart H of the patient P displayed on the display device 3, with the result that the current position of the catheter 2 relative to the target tissue Z to be treated in the heart H of the patient P is available at all times to the physician performing the medical intervention.

In the case of the present exemplary embodiment, the acceleration sensor has a plurality of measured value recorders in order to determine the accelerations in a specific spatial direction in each case or in a specific rotational direction in each case. It is, however, also possible for the acceleration sensor to have only one measured value recorder for recording a movement in a specific spatial direction or in a specific rotational direction, in particular if only one movement in a specific spatial direction or in a specific rotational direction is anticipated. However, instead of one or more acceleration sensors having a plurality of measured value recorders, a plurality of acceleration sensors, each having only one measured value recorder for recording a movement in a spatial direction or in a rotational direction, can also be disposed in or on the catheter 2. As a further alternative it is possible to dispose acceleration sensors, not in or on the catheter 2 itself, but in proximity to the catheter 2, for example on the body surface O of the patient P close to the catheter 2. In this case the acceleration sensors 19 do not have to be directly visible, but can be disposed e.g. on the skin of the patient P under a sterile cover. Acceleration sensors 19 of said kind are illustrated in the FIGURE. These acceleration sensors 19 can also have only one measured value recorder in each case or else a plurality of measured value recorders. For the purpose of recording the movement of the catheter 2, only the acceleration sensor 9 and if necessary further acceleration sensors disposed in or on the catheter 2, only the acceleration sensors 19 disposed in proximity to the catheter 2, or the acceleration sensors 19 disposed in proximity to the catheter 2 and the acceleration sensors 9 disposed in or on the catheter 2 can be used.

The medical instrument does not necessarily have to be a catheter. Instead, the medical instrument can also be a puncture needle or another instrument which can be introduced into the body, an endoscope for example.

Furthermore, the position detection system can also be an optical position detection system which is used primarily when the instrument at least partially protrudes from the inside of the patient's body, so that optical reference markers can be disposed on the instrument.

For the rest, the use of the device and the instrument is not restricted to the heart.

The invention claimed is:

1. A medical intervention device, comprising:
a medical instrument that performs an intervention on a moving tissue of a patient positioned on a patient position device;
a position detection system that determines position data for a position of the medical instrument in a body of the patient, wherein the position detection system comprises an electromagnetic sensor and a transmitter disposed on the patient position device that generates an electromagnetic field for detecting the position of the medical instrument in a coordinate system assigned to the position detection system;
an acceleration sensor that records a movement of the medical instrument caused by involuntary movement of the moving tissue of the patient in a coordinate system assigned to the acceleration sensor;
a computing device that:
synchronizes the position data determined by the position detection system and the movement of the medical instrument recorded by the acceleration sensor for correcting the position data of the medical instrument determined by the position detection system with the movement of the medical instrument recorded by the acceleration sensor, and
superimposes the corrected position data of the medical instrument and an image of the medical instrument onto an image of the moving tissue of the patient; and
a display device that displays the superimposed image comprising the corrected position data of the medical instrument relative to a target tissue to be treated in the moving tissue of the patient to an physician performing the intervention.

2. The medical intervention device as claimed in claim 1, wherein the acceleration sensor comprises a measured value recorder for recording the movement of the medical instrument in a spatial direction or in a rotational direction.

3. The medical intervention device as claimed in claim 1, wherein the acceleration sensor comprises a plurality of measured value recorders and each of the measured value recorders records the movement of the medical instrument in a spatial direction or in a rotational direction.

4. The medical intervention device as claimed in claim 1, further comprising a plurality of acceleration sensors.

5. The medical intervention device as claimed in claim 4, wherein at least one of the acceleration sensors is disposed on or in the medical instrument.

6. The medical intervention device as claimed in claim 4, wherein at least one of the acceleration sensors is disposed on a body surface of the patient.

7. The medical intervention device as claimed in claim 1, wherein the electromagnetic sensor is disposed in or on the medical instrument.

8. The medical intervention device as claimed in claim 1, wherein the medical instrument comprises a catheter or a puncture needle.

9. A medical instrument for performing a medical intervention on a moving tissue of a patient, comprising:
a position detection system that determines a position of the medical instrument in a body of the patient positioned on a patient position device, wherein the position detection system comprises an electromagnetic sensor and a transmitter disposed on the patient position device that generates an electromagnetic field for detecting the position of the medical instrument in a coordinate system assigned to the position detection system;
an acceleration sensor that records a movement of the medical instrument caused by involuntary movement of tissue of the patient in a coordinate system assigned to the acceleration sensor;
a computing device that:
synchronizes the position data determined by the position detection system and the movement of the medical instrument recorded by the acceleration sensor for correcting the position data of the medical instrument determined by the position detection system with the movement of the medical instrument recorded by the acceleration sensor, and
superimposes the corrected position data of the medical instrument and an image of the medical instrument onto an image of the moving tissue of the patient; and a display device that displays the superimposed image comprising the corrected position data of the medical instrument relative to a target tissue to be treated in the moving tissue of the patient to an ph si performing the intervention.

10. The medical instrument as claimed in claim 9, wherein the acceleration sensor comprises a measured value recorder for recording the movement of the medical instrument in a spatial direction or in a rotational direction.

11. The medical instrument as claimed in claim 9, wherein the acceleration sensor comprises a plurality of measured value recorders and each of the measured value recorders records the movement of the medical instrument in a spatial direction or in a rotational direction.

12. The medical instrument as claimed in claim 9, wherein the medical instrument comprises a catheter or puncture needle.

13. The medical instrument as claimed in claim 9, wherein the acceleration sensor is disposed at, in or on a tip region of the medical instrument.

14. A method for operating a medical instrument performing a medical intervention on a moving tissue of a patient, comprising:
  determining position data of the medical instrument in a body of the patient by a position detection system during the medical intervention, wherein the position detection system comprises an electromagnetic sensor and a transmitter disposed on the patient position device that generates an electromagnetic field for detecting the position of the medical instrument in a coordinate system assigned to the position detection system;
  recording a movement of the medical instrument caused by involuntary movement of the moving tissue of the patient by an acceleration sensor in a coordinate system assigned to the acceleration sensor; and
  synchronizing the position data determined by the position detection system and the movement of the medical instrument recorded by the acceleration sensor for correcting the position data of the medical instrument determined by the position detection system with the movement of the medical instrument recorded by the acceleration sensor by a computing device;
  superimposing the corrected position data of the medical instrument and an image of the medical instrument onto an image of the moving tissue of the patient by the computing device; and
  displaying the superimposed image comprising the corrected position data of the medical instrument relative to a target tissue to be treated in the moving tissue of the patient on a display device to an physician performing the intervention.

* * * * *